(12) United States Patent
Blomqvist

(10) Patent No.: US 11,564,588 B2
(45) Date of Patent: Jan. 31, 2023

(54) PROVIDING AN OUTPUT RELATING TO CONDUCTIVITY DISTRIBUTION

(71) Applicant: Nokia Technologies Oy, Espoo (FI)

(72) Inventor: Kim Blomqvist, Espoo (FI)

(73) Assignee: Nokia Technologies Oy, Espoo (FI)

( * ) Notice: Subject to any disclaimer, the term of this patent is extended or adjusted under 35 U.S.C. 154(b) by 458 days.

(21) Appl. No.: 16/527,391

(22) Filed: Jul. 31, 2019

(65) Prior Publication Data

US 2020/0037921 A1 Feb. 6, 2020

(30) Foreign Application Priority Data

Aug. 3, 2018 (EP) ..................................... 18187308

(51) Int. Cl.
*A61B 5/053* (2021.01)
*A61B 5/00* (2006.01)
*A61B 5/0537* (2021.01)

(52) U.S. Cl.
CPC .......... *A61B 5/0537* (2013.01); *A61B 5/4872* (2013.01); *A61B 5/6823* (2013.01); *A61B 2562/0223* (2013.01)

(58) Field of Classification Search
None
See application file for complete search history.

(56) References Cited

U.S. PATENT DOCUMENTS

| | | | | |
|---|---|---|---|---|
| 3,735,247 A * | 5/1973 | Harker | ................. | G01N 27/023 324/226 |
| 4,270,545 A * | 6/1981 | Rodler | ..................... | A61N 1/40 324/225 |
| 4,690,149 A * | 9/1987 | Ko | ....................... | A61B 5/0507 600/409 |
| 4,911,175 A * | 3/1990 | Shizgal | ................ | A61B 5/0537 600/547 |
| 6,359,449 B1 * | 3/2002 | Reining | ................. | G01R 27/08 324/692 |
| 6,374,667 B1 * | 4/2002 | Eriksen | ................ | A61B 5/1073 73/149 |
| 8,423,129 B2 * | 4/2013 | Waffenschmidt | ...... | A61B 5/053 600/547 |
| 9,456,757 B1 * | 10/2016 | Zheng | .................. | A61B 5/7282 |
| 9,733,231 B2 * | 8/2017 | Reitsma | ................. | A61B 5/053 |
| 9,763,593 B2 * | 9/2017 | Eriksen | ................ | A61B 5/1073 |

(Continued)

OTHER PUBLICATIONS

Blomqvist KH, Lundbom J, Lundbom N, Sepponen RE. Body electrical loss analysis (BELA) in the assessment of visceral fat: a demonstration. Biomed Eng Online. Nov. 10, 2011;10:98. doi: 10.1186/1475-925X-10-98. PMID: 22074269; PMCID: PMC3248862. (Year: 2011).*

(Continued)

*Primary Examiner* — Sean P Dougherty
*Assistant Examiner* — Benjamin S Melhus
(74) *Attorney, Agent, or Firm* — Locke Lord LLP

(57) ABSTRACT

An apparatus, method and computer program is described comprising: varying a magnetic field strength of a magnetic field applied to a subject; determining a rate of power loss of the magnetic field, wherein the rate of power loss is a function of the varying magnetic field strength; and providing an output signal based on the determined rate of power loss, wherein the output signal comprises information relating to a conductivity distribution of the subject.

17 Claims, 8 Drawing Sheets

(56) References Cited

U.S. PATENT DOCUMENTS

| | | | | |
|---|---|---|---|---|
| 10,338,055 B2* | 7/2019 | Reitsma | | A61B 5/053 |
| 2003/0055358 A1* | 3/2003 | Ko | | A61B 5/05 |
| | | | | 600/547 |
| 2005/0054939 A1* | 3/2005 | Ben-Ari | | A61B 5/0295 |
| | | | | 600/506 |
| 2005/0065431 A1* | 3/2005 | Reiderman | | A61B 5/055 |
| | | | | 600/415 |
| 2006/0125475 A1* | 6/2006 | Sodickson | | A61B 5/0536 |
| | | | | 324/300 |
| 2006/0142658 A1* | 6/2006 | Perkuhn | | A61B 5/6887 |
| | | | | 600/427 |
| 2007/0241753 A1* | 10/2007 | Sodickson | | G01R 33/3415 |
| | | | | 324/307 |
| 2008/0007275 A1* | 1/2008 | Rubinsky | | G01N 22/04 |
| | | | | 324/694 |
| 2008/0039708 A1* | 2/2008 | Taicher | | A61B 5/055 |
| | | | | 600/410 |
| 2008/0194982 A1* | 8/2008 | Lanfermann | | A61B 5/0522 |
| | | | | 600/547 |
| 2008/0211492 A1* | 9/2008 | Tsukada | | G01R 33/063 |
| | | | | 324/234 |
| 2008/0218180 A1* | 9/2008 | Waffenschmidt | | A61B 5/6887 |
| | | | | 324/633 |
| 2009/0102480 A1* | 4/2009 | Katscher | | A61B 5/0536 |
| | | | | 324/309 |
| 2013/0190588 A1* | 7/2013 | Karo | | A61B 5/0537 |
| | | | | 600/382 |
| 2014/0232403 A1* | 8/2014 | Perkins | | A61B 5/055 |
| | | | | 324/309 |
| 2015/0153431 A1* | 6/2015 | Hancu | | G01R 33/4816 |
| | | | | 324/309 |
| 2015/0374292 A1* | 12/2015 | Wyeth | | A61B 5/05 |
| | | | | 600/409 |
| 2017/0042437 A1* | 2/2017 | Sarhan | | A61B 5/0816 |
| 2017/0319099 A1* | 11/2017 | Levinson | | A61B 5/7214 |
| 2018/0143150 A1* | 5/2018 | Bezemer | | A61B 5/11 |
| 2020/0359898 A1* | 11/2020 | Gleich | | A61B 5/055 |
| 2020/0367795 A1* | 11/2020 | Qian | | A61B 5/6824 |
| 2020/0408866 A1* | 12/2020 | Vesanen | | G01R 33/443 |

OTHER PUBLICATIONS

Blomqvist KH, Sepponen RE. A feasibility study of altered spatial distribution of losses induced by eddy currents in body composition analysis. Biomed Eng Online. Nov. 4, 2010;9:65. doi: 10.1186/1475-925X-9-65. PMID: 21047441; PMCID: PMC2992533. (Year: 2010).*

P. P. Tarjan and R. McFee, "Electrodeless Measurements of the Effective Resistivity of the Human Torso and Head by Magnetic Induction," in IEEE Transactions on Biomedical Engineering, vol. BME-15, No. 4, pp. 266-278, Oct. 1968, doi: 10.1109/TBME.1968.4502577. (Year: 1968).*

H. H. Hu, "Magnetic resonance techniques for fat quantification in obesity," Proceedings of The 2012 Asia Pacific Signal and Information Processing Association Annual Summit and Conference, 2012, pp. 1-10. (Year: 2012).*

* cited by examiner

60

70

PROVIDING AN OUTPUT RELATING TO CONDUCTIVITY DISTRIBUTION

FIELD

The present specification relates to providing an output relating to conductivity distribution of a subject.

BACKGROUND

Non-invasive methods that seek to determine a conductivity distribution of a subject (such as a human body) are known, but there remains a need for alternative arrangements.

SUMMARY

In a first aspect, this specification provides an apparatus comprising: means for varying a magnetic field strength of a magnetic field applied to a subject; means for determining a rate of power loss of the magnetic field, wherein the rate of power loss is a function of the varying magnetic field strength; and means for providing an output signal based on the determined rate of power loss, wherein the output signal comprises information relating to a conductivity distribution of the subject.

In a second aspect, this specification provides an apparatus comprising: a first control module or circuit for varying a magnetic field strength of a magnetic field applied to a subject; a second control module or circuit for determining a rate of power loss of the magnetic field, wherein the rate of power loss is a function of the varying magnetic field strength; and an output for providing an output signal based on the determined rate of power loss, wherein the output signal comprises information relating to a conductivity distribution of the subject.

There may be provided means for determining a body composition of the subject based on at least the conductivity distribution of the subject. The body composition of the subject may comprise information regarding distribution of body tissue. The body composition may, for example, indicate an amount of visceral fat in the subject.

There may be provided means for producing the magnetic field. The means for producing the magnetic field may comprise a tuned or tuneable radio frequency coil. The rate of power loss may be determined based on a change in the voltage across the radio frequency coil or change in the current flowing in coil windings of the radio frequency coil. The means for producing the magnetic field may be configured to surround the subject at an abdominal level of the subject.

The rate of power loss of the magnetic field may be calculated using at least one parameter selected from: conductivity of the radio frequency coil, angular frequency of the magnetic field, magnetic field strength of the magnetic field, radius of the subject, height of the subject, perimeter dimensions of the subject, or dimensions of the radio frequency coil.

There may be provided means for varying angular frequency of the magnetic field, wherein the rate of power loss is also a function of the varying angular frequency.

There may be provided means for determining a water distribution of the subject. Furthermore, there may be provided means for determining a potassium distribution of the subject based at least partially on the water distribution of the subject.

There may be provided means for determining a distribution of intracellular fluid and extracellular fluid.

The means may comprise: at least one processor; and at least one memory including computer program code, the at least one memory and the computer program code configured, with the at least one processor, to cause the performance of the apparatus.

In a third aspect, this specification describes a method comprising: varying a magnetic field strength of a magnetic field applied to a subject; determining a rate of power loss of the magnetic field, wherein the rate of power loss is a function of the varying magnetic field strength; and providing an output signal based on the determined rate of power loss, wherein the output signal comprises information relating to a conductivity distribution of the subject.

The method may comprise determining a body composition of the subject based on at least the conductivity distribution of the subject. The body composition of the subject may comprise information regarding distribution of body tissue. The body composition may, for example, indicate an amount of visceral fat in the subject.

The method may comprise producing the magnetic field (for example, using a radio frequency coil). The rate of power loss may be determined based on a change in the voltage across the radio frequency coil or change in the current flowing in coil windings of the radio frequency coil.

The method may comprise varying angular frequency of the magnetic field, wherein the rate of power loss is also a function of the varying angular frequency.

In a fourth aspect, this specification describes an apparatus configured to perform any method as described with reference to the third aspect.

In a fifth aspect, this specification describes computer-readable instructions (e.g. provided on a computer readable medium, such as a non-transitory computer readable medium) which, when executed by computing apparatus, cause the computing apparatus to perform any method as described with reference to the second aspect.

In a sixth aspect, this specification describes a computer program comprising instructions for causing an apparatus to perform at least the following: varying a magnetic field strength of a magnetic field applied to a subject; determining a rate of power loss of the magnetic field, wherein the rate of power loss is a function of the varying magnetic field strength; and providing an output signal based on the determined rate of power loss, wherein the output signal comprises information relating to a conductivity distribution of the subject.

In a seventh aspect, this specification describes a computer readable medium (e.g. a non-transitory computer readable medium) comprising instructions stored thereon for performing at least one of the following: varying a magnetic field strength of a magnetic field applied to a subject; determining a rate of power loss of the magnetic field, wherein the rate of power loss is a function of the varying magnetic field strength; and providing an output signal based on the determined rate of power loss, wherein the output signal comprises information relating to a conductivity distribution of the subject.

BRIEF DESCRIPTION OF THE DRAWINGS

Example embodiments will now be described, by way of non-limiting examples, with reference to the following schematic drawings, in which.

DETAILED DESCRIPTION

Figure 1:
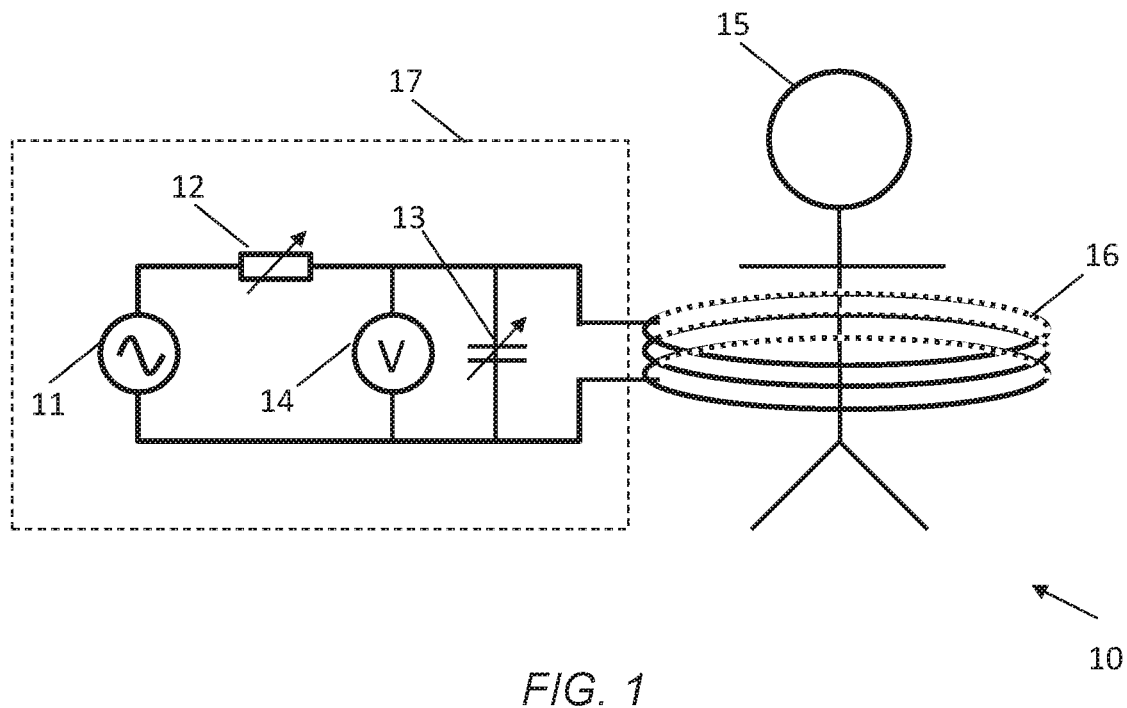
FIG. 1 shows a system in accordance with an example embodiment.

FIG. 1 shows a system, indicated generally by the reference numeral 10, in accordance with an example embodiment. The system m comprises a circuit 17 for applying a magnetic field to a subject, such as subject 15. The circuit 17 may be a resonant circuit forming a voltage divider. The circuit 17 may comprise an alternating current voltage source 11, a variable resistor 12, a voltmeter 14, a variable capacitor 13, and a tuned or tuneable radio frequency coil 16. The radio frequency coil 16 may be used for producing and applying a varying magnetic field to the subject 15 and is an example of a means for producing a magnetic field; other suitable means for producing a magnetic field will be apparent to persons skilled in the art (such as a Helmholtz coil). The alternating current voltage source 11 produces a voltage that may be applied at the radio frequency coil 16 for applying the varying magnetic field to the subject 15. The applied magnetic field may be an oscillating magnetic field. The voltmeter 14 is used for measuring the voltage across the radio frequency coil 16 (which voltage can be used to determine a rate of power loss, as described further below).

Figure 2:
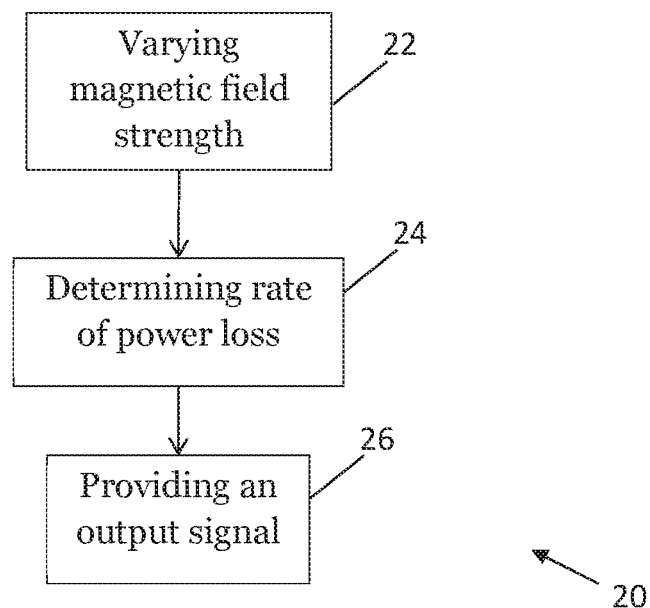
FIG. 2 is a flow chart showing an algorithm in accordance with an example embodiment.

FIG. 2 is a flowchart showing an algorithm, indicated generally by the reference numeral 20, in accordance with an example embodiment. At operation 22, a strength of the time varying magnetic field applied to a subject, such as subject 15, is varied. At operation 24, rate of power loss of the magnetic field is determined. The rate of power loss of the magnetic field may be a function of the varying magnetic field strength. At operation 26, an output signal is provided, wherein the output signal is based on the determined rate of power loss. The output signal may comprise information relating to conductivity distribution of subject 15. The conductivity distribution will be discussed in further detail later in this specification.

In one example embodiment, the magnetic field strength of the magnetic field applied to the subject 15 may be varied by varying the voltage provided by the alternating current voltage source 11.

Figure 3:
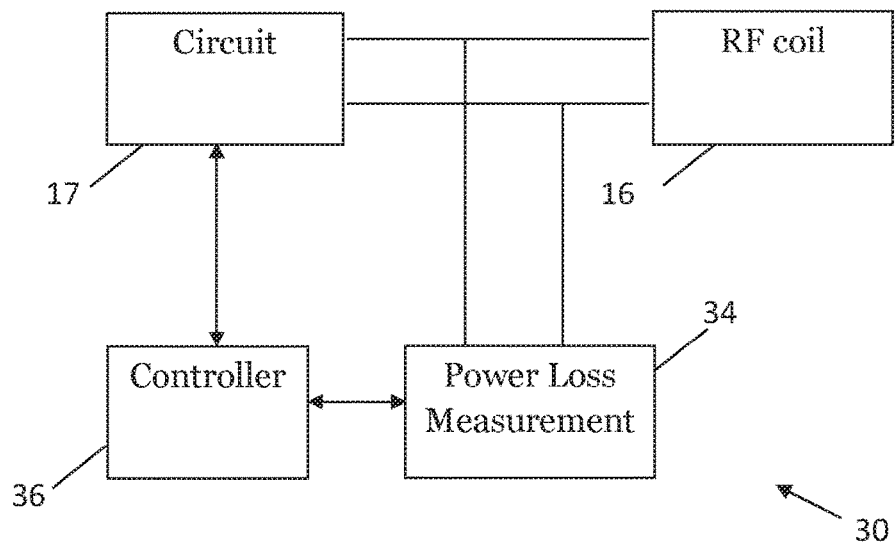
FIG. 3 is a block diagram showing a system in accordance with an example embodiment.

FIG. 3 is a block diagram showing a system, indicated generally by the reference numeral 30, in accordance with an example embodiment. System 30 comprises the circuit 17, the radio frequency coil 16, a controller 36, and a power loss measurement module 34. As shown in FIG. 1, circuit 17 is connected to the radio frequency coil 16. The power loss of the magnetic field caused by the subject within the radio frequency coil 16 is measured at the power loss measurement module 34. The controller 36 sends a signal to the circuit 17 to vary the magnetic field produced by the radio frequency coil 16 (operation 22). As the radio frequency coil 16 surrounds the subject 15, there is power loss in the magnetic field produced by the radio frequency coil 16 due to the conductivity of the subject 15. The power loss measurement module 34 sends information of power loss to the controller 36. The controller 36 then determines a rate of power loss as a function of the varying magnetic field strength (operation 24). Based on the rate of power loss, the controller 36 provides an output signal, such as a slope which is related to the conductivity distribution in the subject 15 (operation 26), e.g. the conductivity distribution in a measured region, such as the abdomen, of the subject 15. In one example embodiment, the power loss measurement module 34 may be comprised within the controller 36.

In an example embodiment, the operations of algorithm 20 are performed twice: a first time without any subject placed inside the radio frequency coil 16 for obtaining reference measurements; and a second time with the subject 15 placed inside the radio frequency coil 16 for obtaining a comparison with the reference measurements. The difference in power loss is determined from the comparison, and may be used for obtaining the conductivity distribution.

As stated earlier, the systems described above may be used for determining the conductivity distribution of the subject 15. The subject 15 placed in the magnetic field perturbs the magnetic field, and the magnitude of this perturbation is measured as the power loss. As different parts of the subject 15 may have different conductivities, a conductivity distribution may be determined based on a measured rate of power loss of the varying magnetic field. In an example embodiment, the following equation may be used for determining power loss:

$$P = \int_r \sigma_{eff} E_{rms}^2 2\pi r h dr$$
$$= \frac{\pi}{8} \sigma_{eff} \omega^2 B^2 r^4 h,$$

P denotes power loss;

$\sigma_{eff}$ denotes effective conductivity;

$E_{rms}$ is the root mean squared (rms) value of the electric field E;

$$E_{rms} = \frac{E_{int}}{\sqrt{2}} = \frac{\omega B r}{2\sqrt{2}},$$

$E_{int}$ denotes an internal electric field circulating at distance of r from a zero axis of a cylinder (in the example above, the subject 15 is assumed to approximate to a cylinder);

r denotes radius of the cylinder;

h denotes height of the cylinder;

ω denotes angular frequency of the magnetic field; and

B denotes magnetic field strength of the magnetic field.

From the above equation, it is shown that when the strength of the magnetic field B is varied, the power loss P varies, and the rate of power loss may then be calculated as a function of the varying magnetic field strength B. The above equation may be specific for cylindrical shaped subjects. As noted above, the shape of subject 15 may be assumed to be cylindrical for purposes of using this equation for determining power loss.

Figure 4:
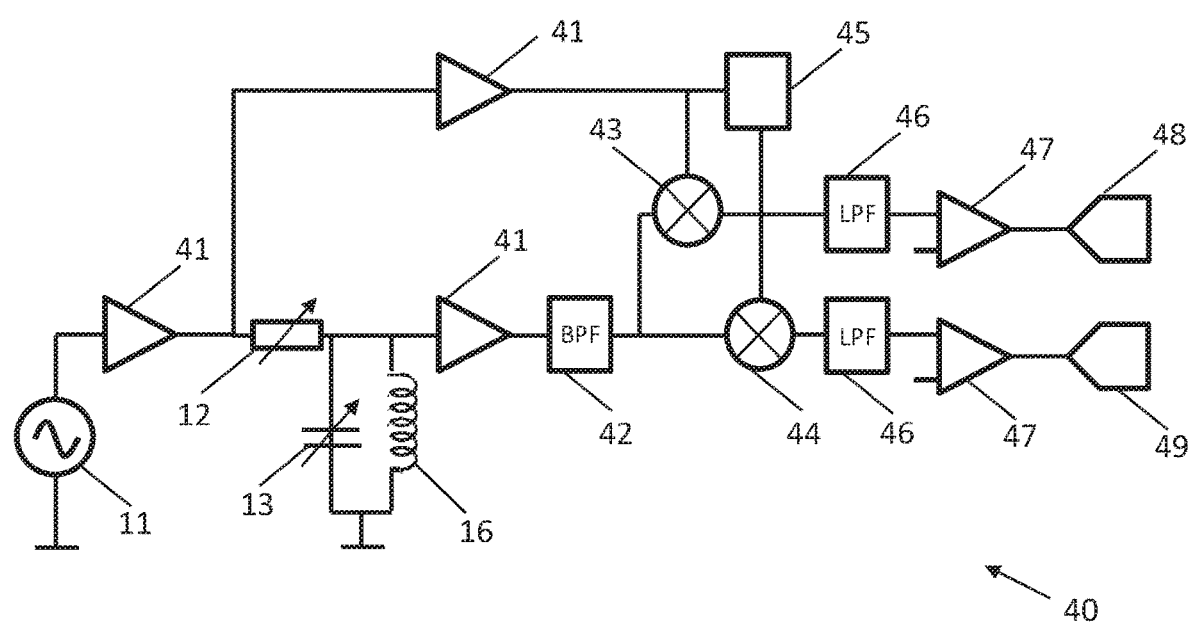
FIG. 4 is a block diagram showing a circuit in accordance with an example embodiment.

FIG. 4 is a block diagram of an example circuit, indicated generally by the reference numeral 40. The circuit 40 may be comprised in the power loss measurement module 34, which may be used for measuring voltage and power loss of the radio frequency coil 16. The circuit 40 may comprise a series resistor (such as series resistor 12), connected to a resonant circuit, similar to circuit 17, to form a voltage divider. The circuit 40 further comprises the alternating current voltage source u, the radio frequency coil 16, variable capacitor 13, buffer amplifiers 41, a band pass filter 42, an in-phase frequency mixer 43, a quadrature frequency mixer 44, a phase-shifter 45, a low pass filters 46, difference amplifiers 47, a real output 48, and an imaginary output 49. A voltage change $\Delta V$ in the voltage divider produced by the change in loss resistance $\Delta R_{loss}$ is calculated approximately as follows:

$$\Delta V = V_0 \left( 6 - 4 \frac{\omega L}{Q} \frac{1}{\Delta R_{loss}} \right)^{-1}$$

$V_o$ denotes the amplitude of the time-varying voltage applied across the voltage divider;
$\omega$ denotes angular frequency of the magnetic field;
L denotes inductance of the radio frequency coil 16;
Q denotes a quality factor; and
$\Delta R_{loss}$ denotes change in loss of resistance.

The resonant circuit is driven from a waveform generator that supports sweeping to locate the resonance frequency. Both the real (48) and imaginary (49) parts of the voltage across the resonant circuit are measured. The value of the voltage ($V_{empty}$) for an empty radio frequency coil 16 is subtracted from the value of the voltage ($V_{loaded}$) of the loaded coil (i.e. with the subject 15 placed inside the radio frequency coil 16) by setting the voltage ($V_{bias}$) of a difference amplifier 47. The voltage difference ($V_{loaded} - V_{empty}$) may be amplified (for example, by sixty times) to get higher sensitivity.

Figure 5:
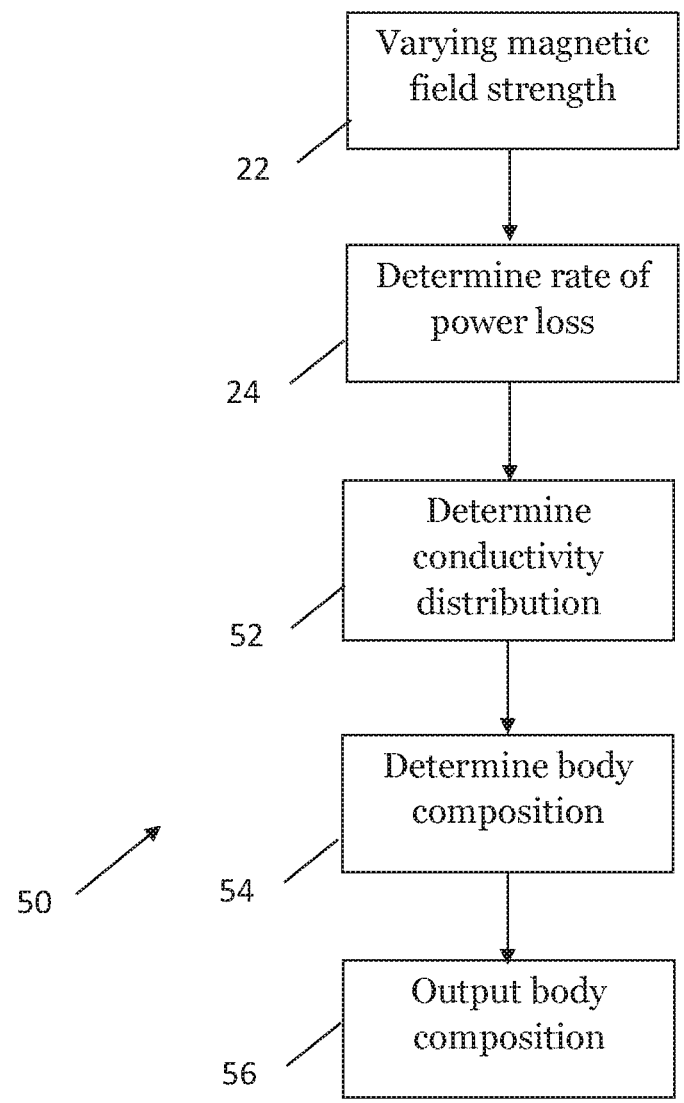
FIG. 5 is a flow chart showing an algorithm in accordance with an example embodiment.

FIG. 5 is a flowchart showing an algorithm, indicated generally by the reference numeral 50, in accordance with an example embodiment. Operations 22 and 24 are same as the operations 22 and 24 of algorithm 20. A magnetic field strength of a magnetic field applied to the subject 15 is varied at operation 22, and rate of power loss is determined at operation 24. At operation 52, a conductivity distribution of the subject 15 is determined based on the rate of power loss with respect to the varying magnetic field strength. The conductivity distribution shows differences in conductivity of different parts of the subject 15. At operation 54, a body composition of the subject 15 is determined based on at least the conductivity distribution of the subject, and the body composition is provided as an output signal at operation 56.

The subject 15 may be a human body. As shown in FIG. 1, the means for producing the magnetic field (the radio frequency coil 16 in that example) is configured to surround the subject 15 at an abdominal level of the subject 15 (a human body in this case). The example embodiments may use bio impedance analysis for determining the body composition. The power loss of the magnetic field is caused by the human abdomen when the magnetic field is applied to the human abdomen. The conductivity distribution may be estimated as a result of the difference in conductivity of the various types of tissue or fluids of the human body. Consequently, the conductivity distribution may be used for determining the body composition of the subject 15. In alternative examples, the subject 15 may also be an animal (such as a pig or a cow), and the example embodiments may be used for estimating body composition (such as volume of fat in comparison with volume of lean meat) of the animal.

In general, a body composition of a human (or animal) body may be used for describing percentages of fat, bone, water, and muscle. A fat free mass or total estimated body fat of the human body may be determined using bioelectrical impedance analysis. The bioelectrical impedance analysis may provide different results at different heights of the body.

The body composition of the subject 15 may be indicative of fat distribution, muscle distribution, water levels, or the like. For example, muscle tissue may have higher electrical conductivity compared to adipose tissue (i.e. fat), and therefore muscle tissue may produce significantly more power loss compared to adipose tissue. When the magnetic field strength of the applied magnetic field is varied (operation 22), the conductivity of adipose tissue is almost constant. In contrast, the conductivity of lean tissue changes as the magnetic field strength is varied. This difference in conductivity may be used to determine a conductivity distribution, which may then be used for determining a body composition. The body composition may indicate an amount visceral fat of the subject 15. The measured rate of power loss may be related to the amount of adipose tissue, such that a small rate of loss would indicate small amount of visceral fat.

Figure 6:
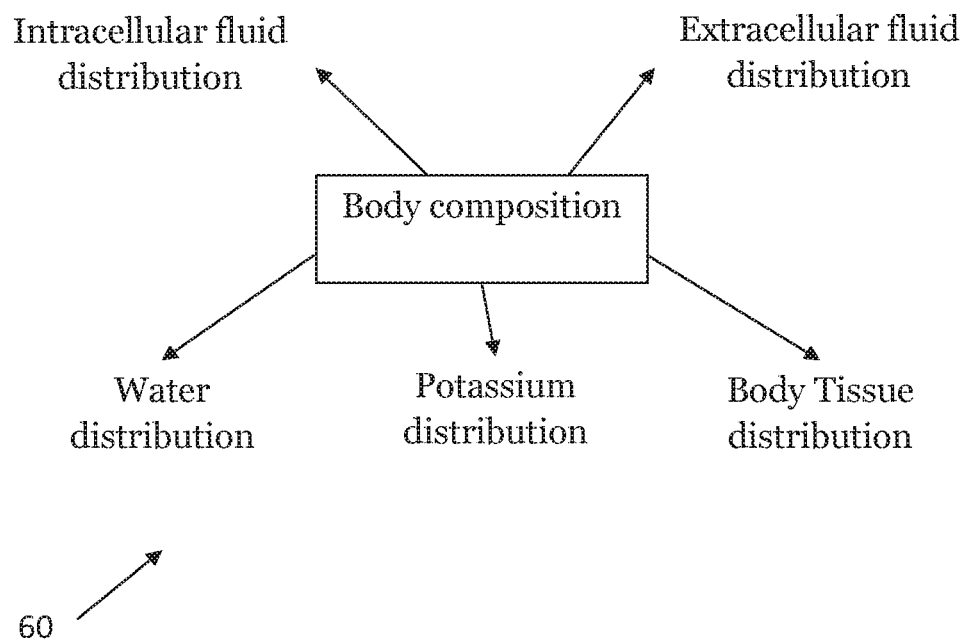
FIG. 6 is a block diagram showing a system in accordance with an example embodiment.

FIG. 6 is a block diagram of a system, indicated generally by the reference numeral 60, in accordance with an example embodiment. The body composition of the subject 15, as determined in algorithm 50, may include information regarding water distribution, potassium distribution, and body tissue distribution. For example, body tissue distribution may indicate accumulation of intra-abdominal fat, water distribution may indicate water content in abdominal muscle walls, and potassium distribution may indicate potassium content in abdominal wall muscles.

In an example, the water distribution is the water distribution in abdominal muscle walls of the subject 15 relative to total water content in an abdominal area of the subject 15. The total water content in the abdominal area of the subject 15 may be determined using bio-electrical impedance analysis. The operations of algorithm 50 may be used for specifically measuring water content in the abdominal muscle walls of the subject 15.

In an example, the potassium distribution is determined at least partially based on the water distribution. The potassium distribution is measured by determining distribution of intracellular fluid and extracellular fluid. This is explained in further detail in FIG. 10.

In an example, in addition to varying the magnetic field strength of the applied magnetic field, the angular frequency of the magnetic field is also varied. This is discussed in further detail in FIG. 10. When the angular frequency is varied, the determined body composition may further include information regarding intracellular fluid distribution and/or extracellular fluid distribution.

Figure 7:
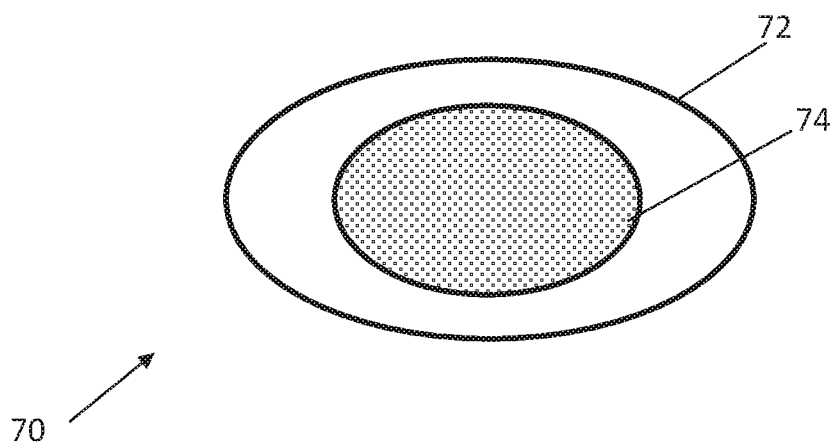
FIG. 7 to FIG. 9 shows example conductivity distributions in accordance with example embodiments.
Figure 8:
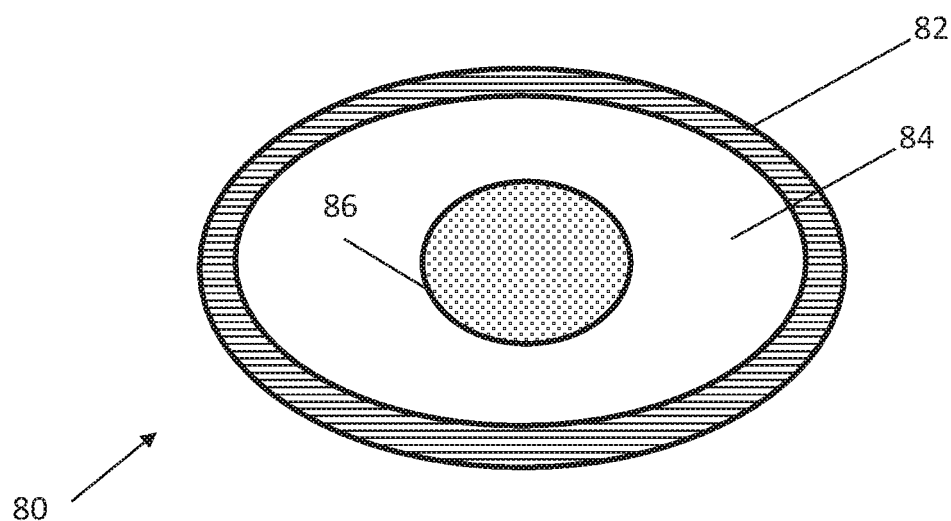
Figure 9:
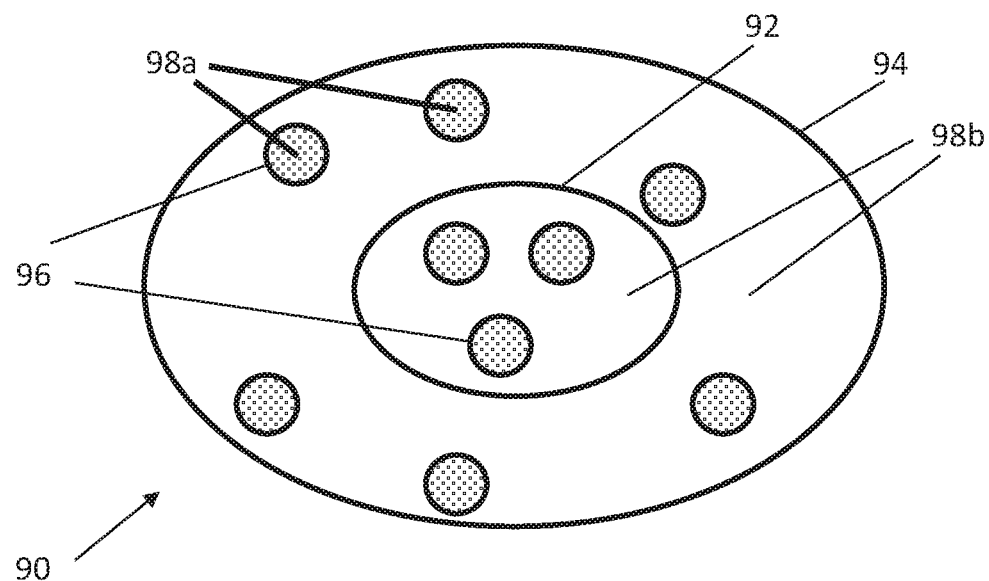

FIG. 7 to FIG. 9 shows example conductivity distributions of a cross-section of the subject 15.

FIG. 7 shows an example conductivity distribution, indicated generally by the reference numeral 70, of the subject 15, in accordance to an example embodiment. When a varying magnetic field is applied to the subject 15 (operation 22), a rate of power loss is determined (operation 24) as a function of the varying magnetic field strength. The conductivity distribution is determined based on the different rates of power loss at different layers, such as layers 72 and 74. Layer 72 may have higher or lower conductivity compared to layer 74, and therefore a conductivity distribution 70 may be obtained due to the differences in rates of power loss at layer 72 and 74.

FIG. 8 shows an example conductivity distribution, indicated generally by the reference numeral 80, of the subject 15, in accordance to an example embodiment. The subject 15 may be a human body, and conductivity distribution 80 may be indicative of the body composition of subject 15. When a varying magnetic field is applied to the subject 15 (operation 22), a rate of power loss is determined (operation 24) as a function of the varying magnetic field strength. The conductivity distribution is determined based on the different rates of power loss at different layers, such as layers 82, 84, and 86. Layer 82 may represent subcutaneous fat (illustrated by striped pattern), layer 84 may represent muscle tissue, and layer 86 may represent visceral fat (illustrated by dotted pattern). As such, the body composition of the subject 15 may be determined, and may indicate the amount of visceral fat in subject 15.

FIG. 9 shows an example conductivity distribution, indicated generally by the reference numeral 90, of the subject 15, in accordance to an example embodiment. The subject 15 may be a human body, and conductivity distribution 90 may be indicative of the body composition of subject 15. The conductivity distribution shows layer 92, layer 94, and plurality of cells 96 (illustrated by dotted circles). The conductivity distribution 90 further illustrates intracellular fluid distribution 98a, and extracellular fluid distribution 98b. The ratio of intracellular fluid with respect to extracellular fluid may indicate the amount of fat in subject 15. For example, high volume of intracellular fluid may indicate less fat volume, and high volume of extracellular fluid may indicate more fat volume. For example, layer 92 may represent visceral fat and layer 94 may represent muscle tissue. The ratio of intracellular fluid with respect to extracellular fluid within layer 92 is lower compared to the ratio of intracellular fluid with respect to extracellular fluid within layer 94. In one example embodiment, the measurement of intracellular fluid and extracellular fluid may be performed by varying angular frequency of the magnetic field applied to the subject 15. This is explained in further detail in FIG. 10.

In an example embodiment the conductivity distribution and/or body composition is provided to and displayed at a screen. The illustration may be similar to the example conductivity distributions 70, 80 and 90. The illustration may be supplemented by text data indicating the body composition, such as amount of visceral fat.

Figure 10:
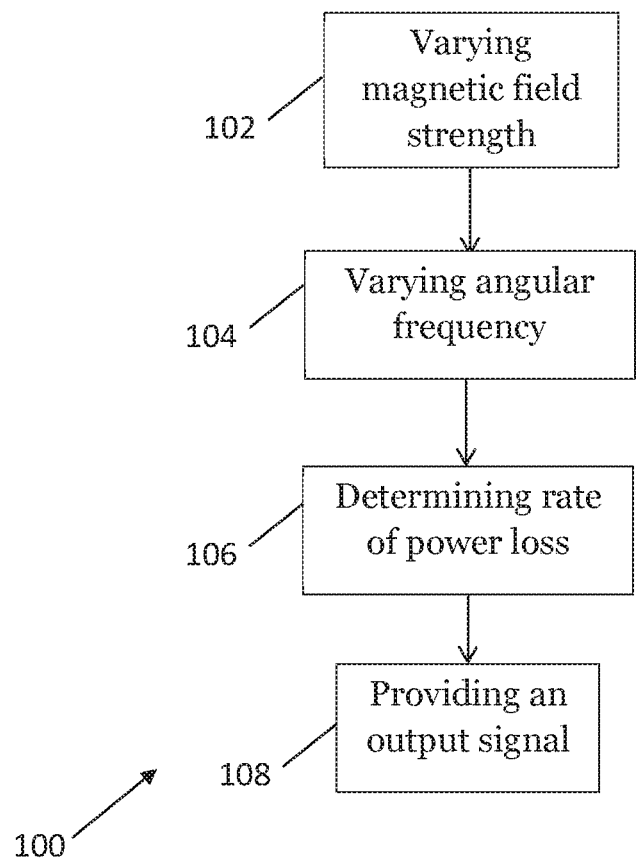
FIG. 10 is a flow chart showing an algorithm in accordance with an example embodiment.

FIG. 10 is a flowchart showing an algorithm, indicated generally by the reference numeral 100, in accordance with an example embodiment. At operation 102, the magnetic field strength of a magnetic field applied to the subject 15 is varied (similar to operation 22). At operation 104, an angular frequency of the magnetic field applied to the subject 15 is varied. At operation 106, a rate of power loss of the magnetic field is determined with respect to the varying magnetic field strength and/or the varying to angular frequency. At operation 108, an output signal is provided based on the rate of power loss.

In an example embodiment, one of the effects of varying angular frequency is that the rate of power loss of the magnetic field may be measured separately for intracellular and extracellular fluid with higher accuracy. This may not be achievable by only varying the magnetic field. For example, each cell (such as the cells 96 shown in FIG. 9) comprises a cell membrane which may act as a capacitor. Varying angular frequency may be used for probing conductivity between intracellular and extracellular volumes of tissue. When a high angular frequency (for example 10 kHz) is used for the magnetic field, the magnetic field may be able to pass through the cell membrane and probe conductivity for intracellular fluid. When a low angular frequency (for example 400 kHz) is used for the magnetic field, the magnetic field may not be able to pass through the cell membrane and may only probe conductivity for extracellular fluid. Therefore, by varying the angular frequency the intracellular fluid distribution and the extracellular fluid distribution may be determined. This may provide a better estimation of the body composition.

Although various aspects of the invention are set out in the independent claims, other aspects of the invention comprise other combinations of features from the described embodiments and/or the dependent claims with the features of the independent claims, and not solely the combinations explicitly set out in the claims.

It is also noted herein that while the above describes various examples, these descriptions should not be viewed in a limiting sense. Rather, there are several variations and modifications which may be made without departing from the scope of the present invention as defined in the appended claims.

Figure 11:
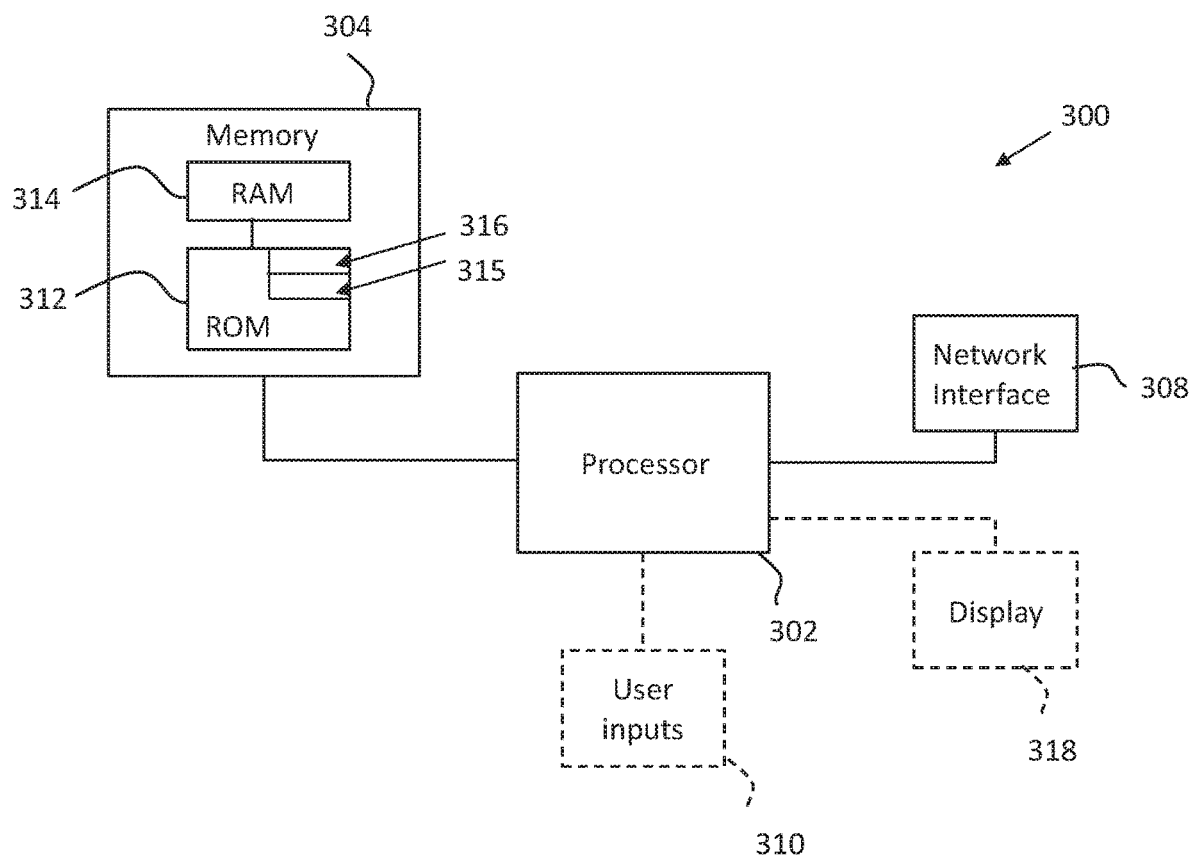
FIG. 11 is a block diagram of a system in accordance with an example embodiment.

For completeness, FIG. 11 is a schematic diagram of components of one or more of the example embodiments described previously, which hereafter are referred to generically as processing systems 300. Processing systems 300 may be used by the controller 36 for performing the operations as disclosed in the example embodiments. A processing system 300 may have a processor 302, a memory 304 closely coupled to the processor and comprised of a RAM 314 and ROM 312, and, optionally, user input 310 and a display 318. The processing system 300 may comprise one or more network/apparatus interfaces 308 for connection to a network/apparatus, e.g. a modem which may be wired or wireless. Interface 308 may also operate as a connection to other apparatus such as device/apparatus which is not network side apparatus. Thus direct connection between devices/apparatus without network participation is possible.

The processor 302 is connected to each of the other components in order to control operation thereof.

The memory 304 may comprise a non-volatile memory, such as a hard disk drive (HDD) or a solid state drive (SSD). The ROM 312 of the memory 314 stores, amongst other things, an operating system 315 and may store software applications 316. The RAM 314 of the memory 304 is used by the processor 302 for the temporary storage of data. The operating system 315 may contain code which, when executed by the processor implements aspects of the algorithms 20, 50, or 100 described above. Note that in the case of small device/apparatus the memory can be most suitable for small size usage i.e. not always hard disk drive (HDD) or solid state drive (SSD) is used.

The processor 302 may take any suitable form. For instance, it may be a microcontroller, a plurality of microcontrollers, a processor, or a plurality of processors.

The processing system 300 may be a standalone computer, a server, a console, or a network thereof. The processing system 300 and needed structural parts may be all inside device/apparatus such as IoT device/apparatus i.e. embedded to very small size In some example embodiments, the processing system 300 may also be associated with external software applications. These may be applications stored on a remote server device/apparatus and may run partly or exclusively on the remote server device/apparatus. These applications may be termed cloud-hosted applications. The processing system 300 may be in communication with the remote server device/apparatus in order to utilize the software application stored there.

Figure 12A:
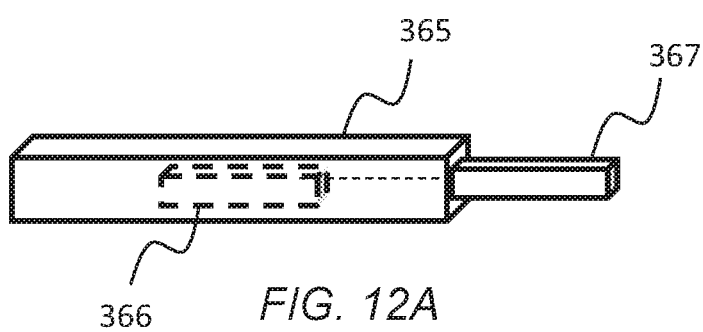
FIGS. 12A and 12B show tangible media, respectively a removable memory unit and a compact disc (CD) storing computer-readable code which when run by a computer perform operations according to example embodiments.
Figure 12B:
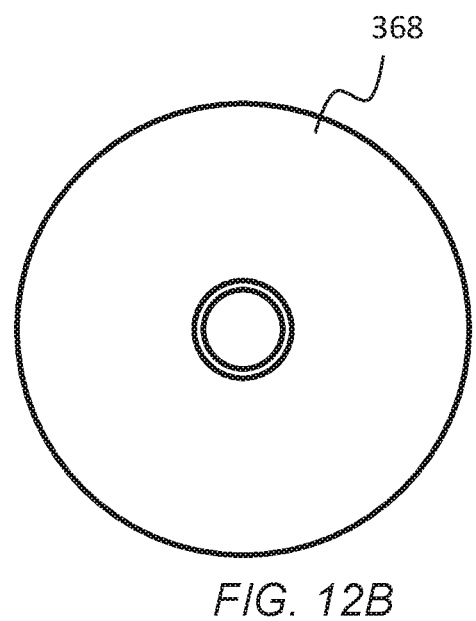

FIGS. 12A and 12B show tangible media, respectively a removable non-volatile memory unit 365 and a compact disc (CD) 368, storing computer-readable code which when run by a computer may perform methods according to example embodiments described above. The removable memory unit 365 may be a memory stick, e.g. a USB memory stick, having internal memory 366 storing the computer-readable code. The memory 366 may be accessed by a computer system via a connector 367. The CD 368 may be a CD-ROM or a DVD or similar. Other forms of tangible storage media may be used. Tangible media can be any device/apparatus capable of storing data/information which data/information can be exchanged between devices/apparatus/network.

Embodiments of the present invention may be implemented in software, hardware, application logic or a combination of software, hardware and application logic. The software, application logic and/or hardware may reside on memory, or any computer media. In an example embodiment, the application logic, software or an instruction set is maintained on any one of various conventional computer-readable media. In the context of this document, a "memory" or "computer-readable medium" may be any non-transitory media or means that can contain, store, communicate, propagate or transport the instructions for use by or in connection with an instruction execution system, apparatus, or device, such as a computer.

Reference to, where relevant, "computer-readable storage medium", "computer program product", "tangibly embodied computer program" etc., or a "processor" or "processing circuitry" etc. should be understood to encompass not only computers having differing architectures such as single/multi-processor architectures and sequencers/parallel architectures, but also specialised circuits such as field programmable gate arrays FPGA, application specify circuits ASIC, signal processing devices/apparatus and other devices/apparatus. References to computer program, instructions, code etc. should be understood to express software for a programmable processor firmware such as the programmable content of a hardware device/apparatus as instructions for a processor or configured or configuration settings for a fixed function device/apparatus, gate array, programmable logic device/apparatus, etc.

As used in this application, the term "circuitry" refers to all of the following: (a) hardware-only circuit implementations (such as implementations in only analogue and/or digital circuitry) and (b) to combinations of circuits and software (and/or firmware), such as (as applicable): (i) to a combination of processor(s) or (ii) to portions of processor(s)/software (including digital signal processor(s)), software, and memory(ies) that work together to cause an apparatus, such as a server, to perform various functions) and (c) to circuits, such as a microprocessor(s) or a portion of a microprocessor(s), that require software or firmware for operation, even if the software or firmware is not physically present.

If desired, the different functions discussed herein may be performed in a different order and/or concurrently with each other. Furthermore, if desired, one or more of the above-described functions may be optional or may be combined. Similarly, it will also be appreciated that the flow diagrams of FIGS. 2, 5, and m are examples only and that various operations depicted therein may be omitted, reordered and/or combined.

It will be appreciated that the above described example embodiments are purely illustrative and are not limiting on the scope of the invention. Other variations and modifications will be apparent to persons skilled in the art upon reading the present specification.

Moreover, the disclosure of the present application should be understood to include any novel features or any novel combination of features either explicitly or implicitly disclosed herein or any generalization thereof and during the prosecution of the present application or of any application derived therefrom, new claims may be formulated to cover any such features and/or combination of such features.

Although various aspects of the invention are set out in the independent claims, other aspects of the invention comprise other combinations of features from the described example embodiments and/or the dependent claims with the features of the independent claims, and not solely the combinations explicitly set out in the claims.

It is also noted herein that while the above describes various examples, these descriptions should not be viewed in a limiting sense. Rather, there are several variations and modifications which may be made without departing from the scope of the present invention as defined in the appended claims.

The invention claimed is:

1. An apparatus comprising:
   at least one processor; and
   at least one memory including computer program code, the at least one memory and the computer program code configured, with the at least one processor, to cause the apparatus to perform,
   varying a magnetic field strength of a magnetic field applied to a subject;
   determining a rate of power loss of the magnetic field due to a conductivity of the subject, wherein the rate of power loss is a function of the varying magnetic field strength; and
   providing an output signal based on the determined rate of power loss, wherein the output signal comprises information relating to a conductivity distribution of the subject,
   the apparatus further comprising a tuned or tuneable radio frequency coil configured to produce the magnetic field, wherein the radio frequency coil is configured to surround a body part of the subject.

2. The apparatus as claimed in claim 1, wherein the at least one memory and the computer program code are configured, with the at least one processor, to cause the apparatus to perform determining a body composition of the subject based on at least the conductivity distribution of the subject.

3. The apparatus as claimed in claim 2, wherein the body composition of the subject comprises information regarding distribution of body tissue.

4. The apparatus as claimed in claim 2, wherein the body composition indicates an amount of visceral fat in the subject.

5. The apparatus as claimed in claim 1, wherein the at least one memory and the computer program code are configured, with the at least one processor, to cause the apparatus to perform producing the magnetic field.

6. The apparatus as claimed in claim 1, wherein the rate of power loss is determined based on a change in the voltage across the radio frequency coil or change in the current flowing in coil windings of the radio frequency coil.

7. The apparatus as claimed in claim 1, wherein the radio frequency coil is configured to surround the subject at an abdominal level of the subject.

8. The apparatus as claimed in claim 1, wherein the rate of power loss of the magnetic field is calculated using at least one parameter selected from: conductivity of a radio frequency coil, angular frequency of the magnetic field, magnetic field strength of the magnetic field, radius of the subject, height of the subject, perimeter dimensions of the subject, or dimensions of the radio frequency coil.

9. The apparatus as claimed in claim 1, wherein the at least one memory and the computer program code are configured, with the at least one processor, to cause the apparatus to perform varying angular frequency of the magnetic field, wherein the rate of power loss is also a function of the varying angular frequency.

10. The apparatus as claimed in claim 9, wherein the at least one memory and the computer program code are configured, with the at least one processor, to cause the apparatus to perform determining a water distribution of the subject.

11. The apparatus as claimed in claim 10, wherein the at least one memory and the computer program code are configured, with the at least one processor, to cause the apparatus to perform determining a potassium distribution of the subject based at least partially on the water distribution of the subject.

12. The apparatus as claimed in claim 9, wherein the at least one memory and the computer program code are configured, with the at least one processor, to cause the apparatus to perform determining a distribution of intracellular fluid and extracellular fluid.

13. A method comprising:
varying a magnetic field strength of a magnetic field applied to a subject, the magnetic field being produced by a tuned or tuneable radio frequency coil configured to surround a body part of the subject;
determining a rate of power loss of the magnetic field due to a conductivity of the subject, wherein the rate of power loss is a function of the varying magnetic field strength; and
providing an output signal based on the determined rate of power loss, wherein the output signal comprises information relating to a conductivity distribution of the subject.

14. The method as claimed in claim 13, further comprising determining a body composition of the subject based on at least the conductivity distribution of the subject.

15. The method as claimed in claim 13, wherein the radio frequency coil is configured to surround the subject at an abdominal level of the subject.

16. A computer program product comprising a non-transitory computer-readable medium having computer-readable code stored thereon, the computer-readable code, when executed by at least one processor, causing an apparatus to perform at least the following:
varying a magnetic field strength of a magnetic field applied to a subject, the magnetic field being produced by a tuned or tuneable radio frequency coil configured to surround a body part of the subject;
determining a rate of power loss of the magnetic field due to a conductivity of the subject, wherein the rate of power loss is a function of the varying magnetic field strength; and
providing an output signal based on the determined rate of power loss, wherein the output signal comprises information relating to a conductivity distribution of the subject.

17. The computer program product as claimed in claim 16, wherein the radio frequency coil is configured to surround the subject at an abdominal level of the subject.

* * * * *